(12) United States Patent
Reszka et al.

(10) Patent No.: US 6,699,850 B2
(45) Date of Patent: Mar. 2, 2004

(54) COMPOSITIONS AND METHODS FOR INHIBITING BONE RESORPTION

(75) Inventors: Alfred A. Reszka, Glenside, PA (US); Edward S. Scolnick, Wynnewood, PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 10/029,678

(22) Filed: Dec. 21, 2001

(65) Prior Publication Data

US 2002/0082244 A1 Jun. 27, 2002

Related U.S. Application Data

(62) Division of application No. 09/336,950, filed on Jun. 21, 1999, now Pat. No. 6,432,931.
(60) Provisional application No. 60/092,919, filed on Jul. 15, 1998, and provisional application No. 60/090,401, filed on Jun. 24, 1998.

(51) Int. Cl.$^7$ ............................................... A61K 31/66
(52) U.S. Cl. ........................ 514/107; 514/108; 514/109
(58) Field of Search ............................... 514/107, 108, 514/109

(56) References Cited

U.S. PATENT DOCUMENTS

| | | | |
|---|---|---|---|
| 3,983,140 A | 9/1976 | Endo et al. | |
| 4,231,938 A | 11/1980 | Monaghan et al. | |
| 4,346,227 A | 8/1982 | Terahara et al. | |
| 4,444,784 A | 4/1984 | Hoffman et al. | |
| 4,518,528 A | 5/1985 | Rasnick | |
| 4,621,077 A | 11/1986 | Rosini et al. | |
| 4,739,073 A | 4/1988 | Kathawala | |
| 4,922,007 A | 5/1990 | Kieczykowski et al. | |
| 4,933,165 A | 6/1990 | Brown | |
| 5,019,651 A | 5/1991 | Kieczykowski | |
| 5,101,068 A | 3/1992 | Palmer | |
| 5,128,328 A | 7/1992 | Zask et al. | |
| 5,157,025 A | 10/1992 | Aberg et al. | |
| 5,177,080 A | 1/1993 | Angerbauer et al. | |
| 5,210,272 A | 5/1993 | Palmer | |
| 5,273,995 A | 12/1993 | Roth | |
| 5,316,765 A | 5/1994 | Folkers et al. | |
| 5,354,772 A | 10/1994 | Kathawala | |
| 5,364,846 A | 11/1994 | Lang et al. | |
| 5,447,922 A | 9/1995 | Lawrence et al. | |
| 5,447,959 A | 9/1995 | Borg | |
| 5,510,517 A | 4/1996 | Dauer et al. | |
| 5,574,025 A | 11/1996 | Anthony et al. | |
| 5,618,964 A | 4/1997 | Cheng et al. | |
| 5,639,653 A | 6/1997 | Bloom et al. | |
| 5,648,491 A | 7/1997 | Dauer et al. | |
| 5,650,523 A | 7/1997 | DeCamp et al. | |
| 5,712,261 A * | 1/1998 | Magnin et al. | ............... 514/75 |
| 5,712,396 A | 1/1998 | Magnin et al. | |
| 5,763,646 A | 6/1998 | Kumar et al. | |
| 5,798,442 A | 8/1998 | Gallant et al. | |
| 5,985,838 A | 11/1999 | Dolle et al. | |
| 6,015,938 A | 1/2000 | Boyle et al. | |
| 6,083,979 A | 7/2000 | Sebti et al. | |

FOREIGN PATENT DOCUMENTS

| | | |
|---|---|---|
| EP | 0 519 748 A2 | 12/1992 |
| JP | 11130670 A | 5/1999 |
| WO | WO 93/16710 | 9/1993 |
| WO | WO 96/31227 | 10/1996 |

OTHER PUBLICATIONS

Sansoni et al., J. of Bone & Min. Res., vol. 10 (1995), pp. 1719–1725, "Inhibition of antigen–presenting cell function by alendronate in vitro".
Henkart, Immunity, vol. 4 (1996), pp. 195–201, "ICE family proteases: mediators of all apoptic cell death?".
Ray et al., Cell, vol. 69 (1992), pp. 597–604, "Viral inhibition of inflammation: cowpow virus encodes an inhibitor of the interleukin–1beta converting enzyme".
Tewari et al., J. of Biol. Chem., vol. 270 (1995), pp. 3255–3260, "Fas– and tumor necrosis factor–induced apoptosis is inhibited by the poxvirus crmA gene product".
Enari et al., Nature, vol. 375 (1995), p. 78–80, "Involvement of an ICE–like protease in Fas–mediated apoptosis".
Villa et al., Trends Biochem. Sci., vol. 22 (1997), pp. 388–393, "Caspases and caspase inhibitors".
Los et al., Nature, vol. 375 (1995), pp. 81–83, "Requirement of an ICE/CED–3 protease for Fas/APO–1–mediated apoptosis".
Enari et al., Nature, vol. 380 (1996), pp. 723–726, "Sequential activation of ICE–like and CPP32–like proteases during Fas–mediated apoptosis".
Woo et al., Bone, vol. 23, No. 5S, p. S549 (1998), "HMG–CoA reductase inhibitors reversibly inhibit fusion on mononucleated preosteoclasts and bone resorption by disrupting actin ring formation".
Coxon et al., Molec. Pharm., vol. 54 (1998), pp. 631–638, "Protein synthesis is required for capase activation and induction of apoptosis by bisphosphonate drugs".
Tan et al., Arthritis & Rheumatism, vol. 31 (1988), pp. 762–766, "Aminobisphosphonate inhibition of interleukin–1–induced bone resorption in mouse calvariae".
Nicholson et al., TIBS, vol. 22 (1997), pp. 299–306, "Caspases: killer proteases".

(List continued on next page.)

Primary Examiner—Theodore J. Criares
(74) Attorney, Agent, or Firm—James M. Hunter, Jr.; Mark R. Daniel

(57) ABSTRACT

The present invention relates to oral compositions and methods for inhibiting bone resoprtion in a mammal while counteracting the occurrence of potentially adverse gastrointestinal effects. The compositions useful herein comprise the combination of a pharmaceutically effective amount of a nitrogen-containing bisphosphonate or a pharmaceutically-acceptable salt thereof and a pharmaceutically effective amount of an isoprenoid compound.

13 Claims, 5 Drawing Sheets

OTHER PUBLICATIONS

Sanders et al., J. of Bone & Min. Res., vol. 13 (1998), pp. 786–792, "Alendronate/interleukin–1beta cotreatment increases interleukin–6 in bone and UMR–106 cells: dose dependence and relationship to th e . . .".

Vitale et al., Endocrinology, vol. 140 (1999), pp. 698–704, "Prenyltransferase inhibitors induce apoptosis inproliferating thyroid cells through a p53–independent, CrmA–sensitive, and caspase–3–like protease– . . .".

Kroon et al., J. of Med., vol. 51 (1997), pp. 16–27, "LDL–cholesterol lowering and atherosclerosis—clinical benefit and possible mechanisms: an update".

Hughes et al., J. of Bone & Min. Res., vol. 10 (1995), pp. 1478–1487, "Bisphosphonates promote apoptosis in murine osteoclasts in vitro and in vivo".

Hughes et al., Bone, vol. 20, No. 4, Abs. No. P362 (1997), "Involvement of the mevalonate pathway in osteoclast apoptosis and the mechanism of action of bisphosphonates".

Luckman et al., Bone, vol. 20, No. 4, Abs. No. P378 (1997), "Bisphosphonates and mevastatin induce apoptosis in J774 macrophages by inhibition of the mevalonate pathway".

Luckman et al., J. of Bone & Min. Res., vol 12, Abs. No. T372 (1997), "Bisphosphonates act by inhibiting protein prenylation".

Gertz et al., Clin. Pharm. Ther., vol. 58 (1995), pp. 288–298, "Studies of the oral bioavailability of alendronate".

Lufkin et al., Osteoporosis Int'l, vol. 4 (1997), pp. 320–322, "Pamidronate: an unrecognized problem in gastrointestinal tolerability".

Riggs et al., N. Eng. J. of Med., vol. 327 (1992), pp. 620–627, "The prevention and treatment of osteoporosis".

Yalpani, Chemistry & Industry (1996), pp. 85–89, "Cholesterol–lowering drugs".

Luckman et al., J. of Bone & Min. Res. vol. 13 (1998), pp. 581–589, "Nitrogen–containing bisphosphonates inhibit the mevalonate pathway and prevent post–translational prenylation of GTP–binding proteins . . .".

Gertz et al., Osteoporosis Int'l, Suppl. 3:S13–16 (1993), "Clinical pharmacology of alendronate sodium".

Seltenmeyer et al., J. of Bone & Min. Res., vol. 12, vol. 2, Abst. No. 4S, T376 (1997), "A comparison of the antiresorptive potency of various bisphosphonates in vivo with the inhibitory efferts in vitro on squalene . . .".

Alnemri et al., Cell, vol. 87, pp. 171 (1996), Letter to the Editor: "Human ICE/CED–3 protease nomenclature".

Chole et al., J. of Bone & Min. Res., V1. 10 (1995), pp. 281–284, "In vivo inhibition of localized bone resorption by human recombinant interleukin–1 receptor antagonist".

Chole et al., Calcified Tissue Int'l, vol. 55 (1994), p. 12–15, Laboratory Investigations: Human recombinant interleukin–1 receptor blocks bone resorption induced by interleukin– beta but not interleukin–1 alpha.

Kimble et al., J. Clin. Invest., vol. 93 (1994), pp. 1959–1967, "Interleukin–1 receptor antagonist decreases bone loss and bone resorption in ovariectomized rats".

Hara, Chem Abstracts (1995) 123:306613n, "Osteoporosis inhibitors containing polyisoprenoids".

Rudel, Herz, vol. 24, No. 3 (1999), pp. 236–241, "Caspase inhibitors in prevention of apoptosis".

Wu et al., Methods: A Comparison to Methods in Enzymology, vol. 17, pp. 320–328 (1999), "Irreversible caspase inhibitors: Tools for studying apoptosis".

Fisher et al., Proc. Nat'l. Acad. Sci. USA, vol. 96, pp. 133–138 (1999), "Alendronate mechanism of action: geranylgeraniol, an intermediate in the mevalonate pathway, prevents inhibition of osteoclast formation . . . ".

Hamilton et al., Bioorgan. & Medicinal & Chem. Letters, vol. 8 (1998), pp. 1655–1660, "Synthesis and proteinase inhibitory properties of diphenyl phosphonate analogues of aspartic and glutamic acids".

McGuire et al., Oncogene (1997), vol. 14, pp. 305–312, "Geranylgeraniol potentiates lovastatin inhibition of oncogenic H–Ras processing and signaling while preventing cytotoxicity".

Luckman et al., J. of Bone & Min. Res. (1998), vol. 13, pp. 1668–1678, "Heterocycle–containing bisphosphonates cause apoptosis and inhibit bone resorption by preventing protein prenylation . . . ".

* cited by examiner 34 kDa Mst fragment →

COMPOSITIONS AND METHODS FOR INHIBITING BONE RESORPTION

CROSS-REFERENCE TO RELATED APPLICATIONS

This application is a divisional of U.S. Ser. No. 09/336,950, filed Jun. 21, 1999, now U.S. Pat No. 6,432,931; which claims the benefit of Provisional application No. 60/092,919 filed Jul. 15, 1998 and Provisional application No. 60/090,401 filed Jun. 24, 1998.

BRIEF DESCRIPTION OF THE INVENTION

The present invention relates to oral compositions and methods for inhibiting bone resorption in a mammal while counteracting potential adverse gastrointestinal effects. The compositions useful herein comprise the combination of a pharmaceutically effective amount of a nitrogen-containing bisphosphonate or a pharmaceutically-acceptable salt thereof and a pharmaceutically effective amount of an isoprenoid compound.

BACKGROUND OF THE INVENTION

A variety of disorders in humans and other mammals involve or are associated with abnormal bone resorption. Such disorders include, but are not limited to, osteoporosis, Paget's disease, periprosthetic bone loss or osteolysis, and hypercalcemia of malignancy. The most common of these disorders is osteoporosis, which in its most frequent manifestation occurs in postmenopausal women. Osteoporosis is a systemic skeletal disease characterized by a low bone mass and microarchitectural deterioration of bone tissue, with a consequent increase in bone fragility and susceptibility to fracture. Osteoporotic fractures are a major cause of morbidity and mortality in the elderly population. As many as 70% of women and a third of men will experience an osteoporotic fracture. A large segment of the older population already has low bone density and a high risk of fractures. There is a significant need to both prevent and treat osteoporosis and other conditions associated with bone resorption. Because osteoporosis, as well as other disorders associated with bone loss, are generally chronic conditions, it is believed that appropriate therapy will typically require chronic treatment.

Multinucleated cells called osteoclasts are responsible for causing bone loss through a process known as bone resorption. It is well known that bisphosphonates are selective inhibitors of osteoclastic bone resorption, making these compounds important therapeutic agents in the treatment or prevention of a variety of generalized or localized bone disorders caused by or associated with abnormal bone resorption. See H. Fleisch, *Bisphosphonates In Bone Disease, From The Laboratory To The Patient*, 3rd Edition, Parthenon Publishing (1997), which is incorporated by reference herein in its entirety. Without being limited by theory, it is believed that bisphosphonates inhibit osteoclast function by triggering apoptosis, i.e. programmed cell death. See D. E. Hughes et al., "Bisphosphonates promote apoptosis in murine osteoclasts in vitro and in vivo", *Journal of Bone and Mineral Research*, 10 (10), 1478–1487, 1995, which is incorporated by reference herein in its entirety.

At present, a great amount of preclinical and clinical data exists for the potent aminobisphosphonate compound alendronate. Evidence suggests that other nitrogen-containing bisphosphonates such as pamidronate, risedronate, ibandronate and zolendronate, have many properties in common with alendronate, including high potency as inhibitors of osteoclastic bone resorption.

Despite their therapeutic benefits, bisphosphonates are poorly absorbed from the gastrointestinal tract. See B. J. Gertz et al., *Clinical Pharmacology of Alendronate Sodium, Osteoporosis Int.*, Suppl. 3: S13–16 (1993) and B. J. Gertz et al., *Studies of the oral bioavailability of alendronate, Clinical Pharmacology & Therapeutics*, vol. 58, number 3, pp. 288–298 (September 1995), which are incorporated by reference herein in their entirety. Intravenous administration has been used to overcome this bioavailability problem. However, intravenous administration is costly and inconvenient, especially when the patient must be given an intravenous infusion lasting several hours on repeated occasions.

If oral administration of the bisphosphonate is desired, relatively high doses must be administered to compensate for the low bioavailability from the gastrointestinal tract. To offset this bioavailability problem, it is generally recommended that the patient take the bisphosphonate on an empty stomach and fast for at least 30 minutes afterwards. However, many patients find the need for such fasting on a daily basis to be inconvenient. Moreover, oral administration has been associated with adverse gastrointestinal effects, especially those relating to the esophagus. See Fleisch, Id. These effects appear to be related to the irritant potential of the bisphosphonate in the esophagus, a problem which is exacerbated by the presence of refluxed gastric acid. Without being limited by theory, it is believed that the potential gastrointestinal effects of oral bisphosphonates is related to the induction of apoptosis, i.e. programmed death, of the cells of the epithelial lining of the gastrointestinal tract.

For example, the bisphosphonate, pamidronate has been associated with esophageal ulcers. See E. G. Lufkin et al., *Pamidronate: An Unrecognized Problem in Gastrointestinal Tolerability, Osteoporosis International*, 4: 320–322 (1994), which is incorporated by reference herein in its entirety. Although not as common, the use of alendronate has been associated with esophagitis and/or esophageal ulcers. See P. C. De Groen, et al., *Esophagitis Associated With The Use Of Alendronate, New England Journal of Medicine*, vol. 335, no. 124, pp. 1016–1021 (1996), D. O. Castell, *Pill Esophagitis—The Case of Alendronate, New England Journal of Medicine*, vol. 335, no. 124, pp. 1058–1059 (1996), and U. A. Liberman et al., *Esophagitis and Alendronate, New England Journal of Medicine*, vol. 335, no. 124, pp. 1069–1070 (1996), which are incorporated by reference herein in their entirety. The degree of adverse gastrointestinal effects of bisphosphonates has been shown to increase with increasing dose. See C. H. Chestnut et al., *Alendronate Treatment of the Postmenopausal Osteoporotic Woman: Effect of Multiple Dosages on Bone Mass and Bone Remodeling, The American Journal of Medicine*, vol. 99, pp. 144–152, (August 1995), which is incorporated by reference herein in its entirety. Also, these adverse esophageal effects appear to be more prevalent in patients who do not take the bisphosphonate with an adequate amount of liquid or who lie down shortly after dosing, thereby increasing the chance for esophageal reflux.

Bisphosphonate treatment regimens normally involve the chronic administration of relatively low doses of the bisphosphonate compound, with the objective of delivering the desired cumulative therapeutic dose over the course of the treatment period. However, chronic dosing, especially chronic daily dosing, can have the disadvantage of causing adverse gastrointestinal effects due to the repetitive, continuous, and additive irritation to the gastrointestinal tract. This potential problem can therefore interfere with patient compliance, and in severe cases even require cessation of treatment. Therefore, it is seen that there is a need to minimize the potential adverse effects that can be associated with bisphosphonate bone resorption therapy.

Isoprenoids are compoounds that are constructed from the five-carbon building block isoprene, which is also known as 2-methyl-1,3-butadiene. Compounds comprising two or more isoprene units are known as terpenes. Examples of isoprenoids and terpenes include 3,3-dimethyl-2-butan-1-ol (a five-carbon compound), geraniol (a ten-carbon compound), farnesol (a fifteen-carbon compound), and geranylgeraniol (a twenty-carbon compound). See Lehninger, A. L., *Biochemistry*, 1975, pp. 296, and 682–683, which is incorporated by reference herein in its entirety.

For example, geranylgeraniol is a linear terpene containing four isoprene units, corresponding to the following chemical structure.

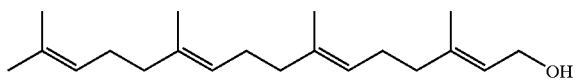

The geranylgeraniol derivative, geranylgeranyl pyrophosphate is an intermediate in the cholesterol biosynthetic pathway and is a substrate in the prenylation of proteins. See J. A. Glomset et l., *Geranylgeranylated proteins, Biochem-Soc-Trans.*, 1992 May, 20(2): 479–484, which is incorporated by reference herein in its entirety.

It is found in the present invention that isoprenoids block the bisphosphonate-induced inhibition of osteoclast function. For example, in osteoclast cell cultures and bone resorption assays, isoprenoids such as geranylgeraniol can block the inhibitory effect that would otherwise be observed with a bisphosphonate such as alendronate monosodium trihydrate. In the osteoclasts, it is believed that nitrogen-containing bisphosphonates trigger the cleavage of a kinase known as Mst (mammalian Sterile-20-like kinase). At least two isoforms of Mst are known, i.e. "Mst 1" and "Mst 2". See, Taylor et al., "Newly identified stress-responsive protein kinases, Krs-1 and Krs-2", *Proc. Natl. Acad. Sci. USA*, Vol. 93 (1996), pp. 10099–10104; Creasy et al., "Cloning and characterization of a human protein kinase with homology to Ste20," *The J. of Biological Chemistry*, Vol. 270, No. 37 (1995), pp. 21695–21700; Creasy et al., "Cloning and characterization of a member of the MST subfamily of Ste20-like kinases", *Gene*, Vol. 167 (1995), pp. 303–306; Creasy et al., "The Ste 20-like protein kinase, Mst 1, dimerizes and contains an inhibitory domain", *The J. of Biological Chemistry*, Vol. 271, No. 35 (1996), pp. 21049–21053; and Wang and Erikson, "Activation of protein serine/threonine kinases p42, p63, and p87 in Rous sarcoma virus-transformed cells: signal transduction/transformation-dependent MBP kinases", *Mol. Biol. Cell*, 3, pp. 1329–1337 (1992), which are all incorporated by reference herein in their entirety. Mst cleavage is known to be triggered by cellular stress events, and is associated with apoptosis. See Graves et al., EMBO Journal, 17, 2224–2234, 1998, which is incorporated by reference herein in its entirety. An isoprenoid such as geranylgeraniol, however, is found to prevent the cleavage of Mst that is induced by bisphosphonates such as alendronate monosodium trihydrate. However, isoprenoids have not previously been investigated either in vitro or in vivo for their ability to mitigate the potentially adverse gastrointestinal side effects that can be associated with bisphosphonate anti-bone resorption therapy.

In the present invention, the combination of a nitrogen-containing bisphosphonate or a pharmaceutically-acceptable salt thereof and an isoprenoid compound is highly effective for inhibiting bone resorption while mitigating the potentially adverse gastrointestinal effects that can be associated with bisphosphonate therapy. The combination has the advantage of providing increased safety and better patient compliance, which should maximize therapeutic efficacy. Without being limited by theory it is believed that the isoprenoid compound blocks the potentially harmful effect of the bisphosphonate on the epithelial cells of the gastrointestinal tract. By selecting an appropriate dosage of the isoprenoid compound it is possible to orally deliver a sufficiently high local concentration of the isoprenoid compound to the gastrointestinal tract to block the potentially harmful effects of the nitrogen-containing bisphosphonate, while minimizing the blocking effect on the osteoclasts, where the full therapeutic benefit of the bisphosphonate is desired to inhibit bone resorption.

It is an object of the present invention to provide compositions comprising the combination of a nitrogen-containing bisphosphonate or a pharmaceutically-acceptable salt thereof and an isoprenoid compound.

It is another object of the present invention to provide improved oral methods for inhibiting bone resorption and the conditions associated therewith in a mammal, particularly wherein said mammal is a human.

It is another object of the present invention to provide improved oral methods for treating or preventing abnormal bone resorption and the conditions associated therewith.

It is another object of the present invention to provide such oral methods while counteracting potential adverse gastrointestinal effects.

It is another object of the present invention to provide such methods wherein the dosing is maintained until the desired therapeutic effect is achieved.

It is another object of the present invention to treat or prevent abnormal bone resorption in an osteoporotic mammal, preferably an osteoporotic human.

These and other objects will become readily apparent from the detailed description which follows.

SUMMARY OF THE INVENTION

The present invention relates to a pharmaceutical composition comprising a nitrogen-containing bisphosphonate or pharmaceutically acceptable salt thereof and an isoprenoid compound.

In further embodiments the present invention relates to a pharmaceutical composition comprising a pharmaceutically-effective amount of a nitrogen-containing bisphosphonate or phamraceutically acceptable salt thereof and an amount of an isoprenoid compound effective to counteract nitrogen-containing bisphosphonate-associated gastrointestinal effects.

In further embodiments, the present invention relates to a method for inhibiting bone resorption in a mammal in need thereof comprising administering a nitrogen-containing bisphosphonate or pharmaceutically acceptable salt thereof and an isoprenoid compound.

In further embodiments, the present invention relates to a method for inhibiting bone resorption in a mammal in need thereof comprising sequentially administering an isoprenoid compound and a ntirogen-containing bisphosphonate or pharmaceutically acceptable salt thereof.

In further embodiments, the present invention relates to the use of a composition in the manufacture of a medicament for inhibiting bone resorption in a mammal in need thereof, said composition comprising a nitrogen-containing bisphosphonate or pharmaceutically acceptable salt thereof and an isoprenoid compound.

In further embodiments, the present invention relates to the use of a composition comprising a nitrogen-containing bisphosphonate or pharmaceutically acceptable salt thereof and an isoprenoid compound for inhibiting bone resoprtion in a mammal in need thereof.

All percentages and ratios used herein, unless otherwise indicated, are by weight. The invention hereof can comprise, consist of, or consist essentially of the essential as well as optional ingredients, components, and methods described herein.

DETAILED DESCRIPTION OF THE INVENTION

Figure 1:
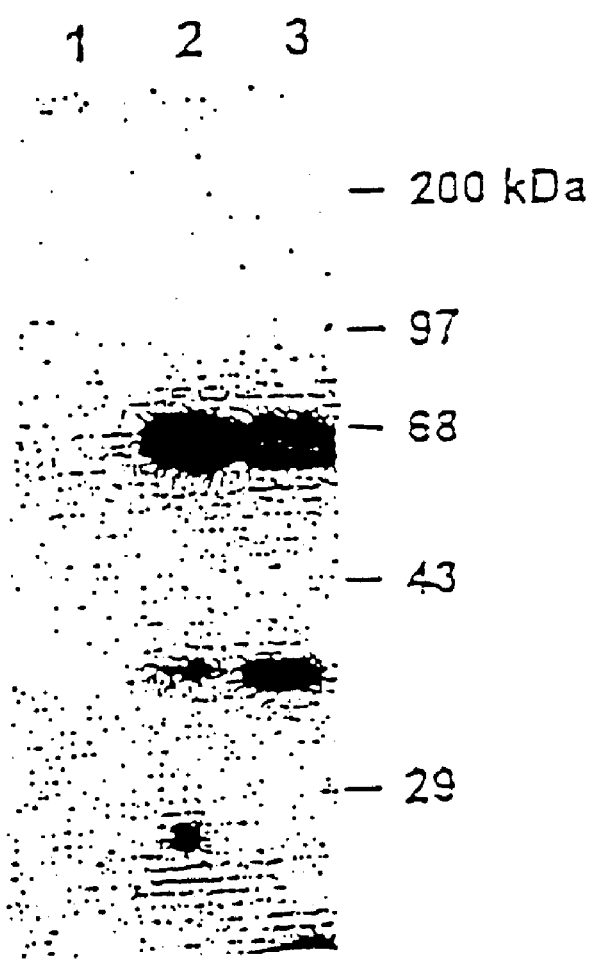
FIG. 1 shows the identification of a 34 kDa Mst kinase fragment that is activated by 30 μM alendronate monosodium trihydrate (a nitrogen-containing bisphosphonate). The 34 kDa Mst kinase fragment is an amino-terminal cleavage product of Mst. Osteoclast-like cells are isolated and treated with alendronate monosodium trihydrate. Cell lysates are exposed to treatment with a cocktail of commercially available anti-Mst and anti-Krs antibodies that recognize the amino-terminus of Mst kinase and Protein A-agarose beads to immunoprecipitate Mst from the samples. The samples are analyzed using an in-gel kinase assay. These data demonstrate that the anti-Mst and anti-Krs antibody cocktail immunoprecipitates 59 and 60 kDa Mst Kinases as well as a 34 kDa Mst Kinase fragment in untreated osteoclasts (lane 2) and alendronate monosodium tirhydrate-treated osteoclasts (lane 3). No kinase activities are immnunoprecipitated in the absence of anti-Mst and anti-Krs antibodies (lane 1). These data also demonstrate that the 34 kDa Mst Kinase fragment immunoprecipitated by the anti-Mst and anti-Krs antibody cocktail is activated by alendronate monosodium trihydrate (lane 3).
Figure 2:
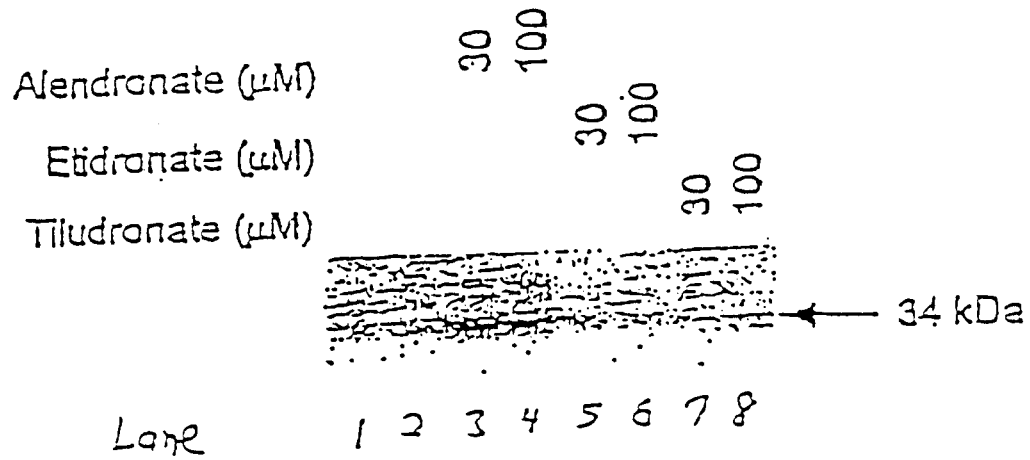
FIG. 2 shows the preferential response of a 34 kDa Mst Kinase fragment to alendronate monosodium trihydrate (a nitrogen-containing bisphosphonate) versus etidronate disodium or tiludronate disodium (both of which are non-nitrogen-containing bisphosphonates). Osteoclast like cells are treated with alendronate monosodium trihydrate, etidronate disodium, or tiludronate disodium at concentrations of both 30 μM and 100 μM for about 17 hours. Kinase activities are analyzed using an in-gel kinase assay. Autoradiographs are developed after film exposure for several days. These data show the activation of the 34 kDa Mst Kinase fragment by alendronate monosodium trihydrate at either 30 μM (lane 3) or 100 μM (lane 4). Equivalent doses of etidronate disodium (lanes 5 and 6) or tiludronate disodium (lanes 7 and 8), fail to activate this kinase fragment, with results being similar to no treatment controls (lanes 1 and 2).
Figure 3:
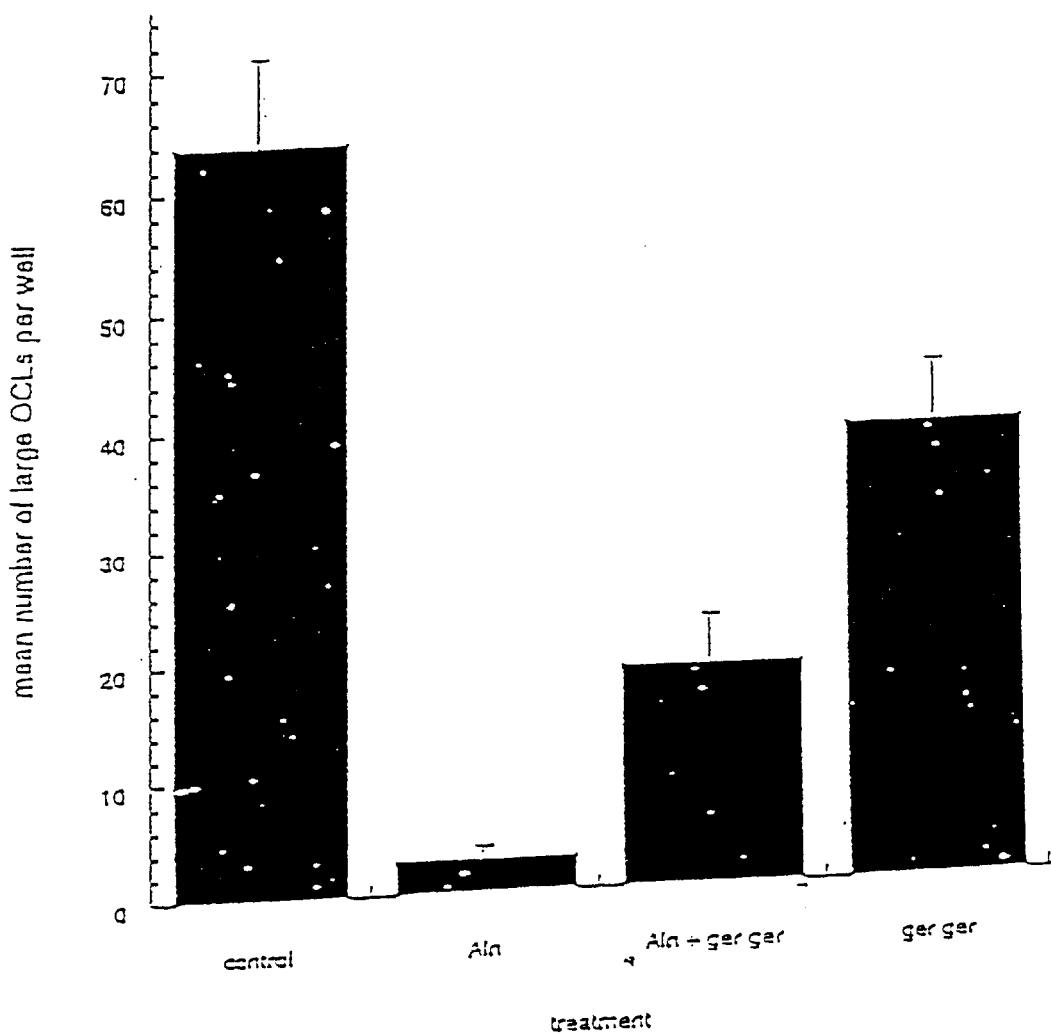
FIG. 3 shows the effect of 15 μM alendronate monosodium trihydrate (a nitrogen-containing bisphosphonate), 10 μM geranylgeraniol, and the combination of 15 μM alendronate monosodium trihydrate and 10 μM geranyl geraniol on osteoclast like cells in terms of the formation of cells larger than 250 μm (as measured in one dimension). The compounds are dosed both 5 and 6 days after establishing the culture, and the formation of 250 μm cells are counted using an inverted microscope with a 10×objective and quantitated versus a no treatment control.
Figure 4:
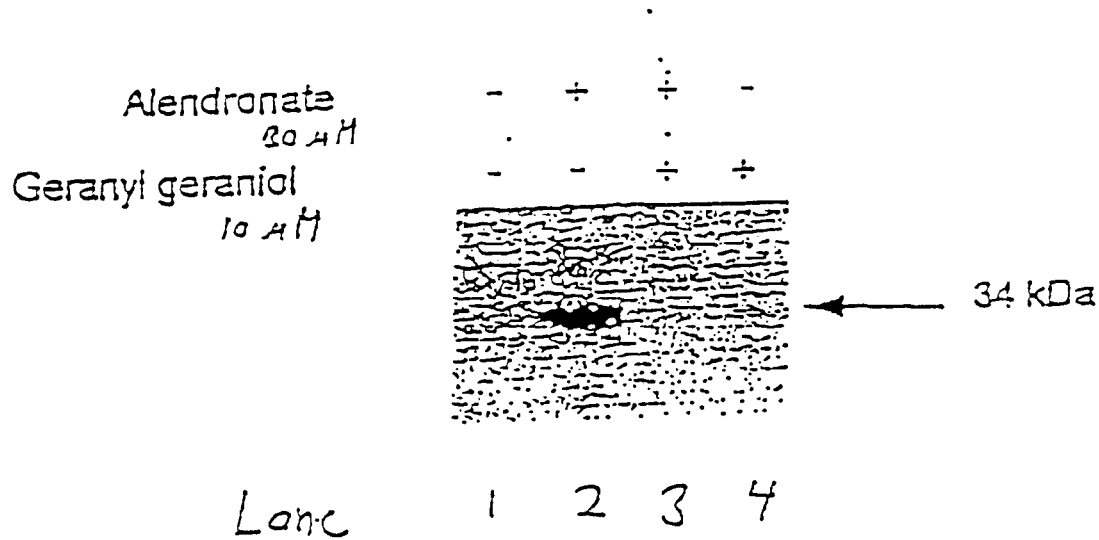
FIG. 4 shows the effect of 10 μM geranylgeraniol on the activation of osteoclast like cells with 30 μM alendronate monosodium trihydrate (a nitrogen-containing bisphosphonate). Lane 1 shows a no treatment control. Lane 2 shows the activation of the 34 kDa Mst Kinase fragment by alendronate monosodium trihydrate. Lane 3 shows that geranylgeraniol negates this activation. Lane 4 is a treatment control with only geranylgeraniol.
Figure 5:
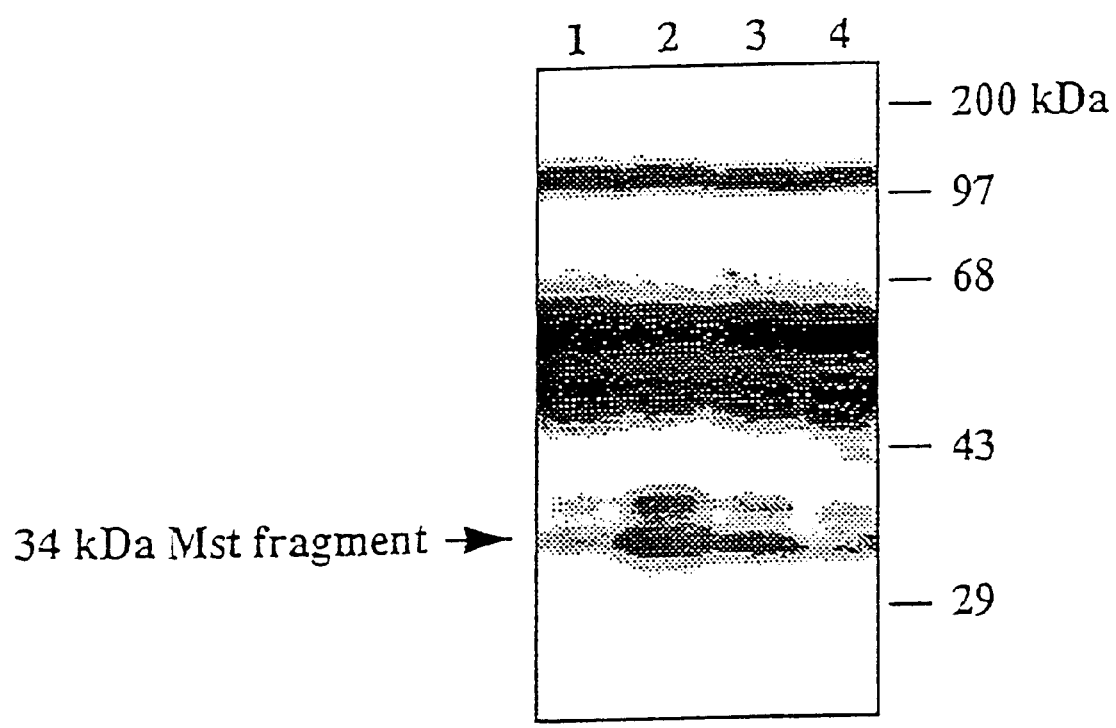
FIG. 5 shows that activation of Mst1 cleavage by 30 μM alendronate monosodium trihydrate is blocked by geranylgeraniol and partially blocked by farnesol. Osteoclast like cells are purified from cocultures by sequential treatment of culture dishes with collagenase and EDTA. After the desired treatment, cell lysates are analyzed by an in-gel kinase assay using myelin basic protein as a substrate. Lane 1 is a no-treatment control. Lane 2 shows treatment with 30 μM alendronate monosodium trihydrate. Lane 3 shows treatment with 30 μM alendronate monosodium trihydrate and 10 μM farnesol. Lane 4 shows treatment with 30 μM alendronate monosodium trihydrate and 10 μM geranylgeraniol.

The present invention relates to compositions and methods for inhibiting bone resorption in a mammal in need of such treatment, while counteracting the occurence of adverse gastrointestinal effects. The compositions comprise a pharmaceutically effective amount of a nitrogen-containing bisphosphonate or a pharmaceutically-acceptable salt thereof and a pharmaceutically effective amount of an isoprenoid compound.

The term "pharmaceutically effective amount", as used herein, means that amount of the nitrogen-containing bisphosphonate compound or isoprenoid compound, that will elicit the desired therapeutic effect or response or provide the desired benefit when administered in accordance with the desired treatment regimen. A prefered pharmaceutically effective amount of the nitrogen-containing bisphosphonate is a bone resorption inhibiting amount. A preferred pharmaceutically effective amount of the isoprenoid compound is an amount that will counteract, i.e. block or mitigate, the occurrence of adverse gastrointestinal effects, while not counteracting, or only minimally counteracting, the therapeutic bone resorption effects of the nitrogen-containing bisphosphonate.

The term "counteracting the occurence of adverse gastrointestinal effects", as used herein, means to prevent, block, decrease, or lessen the occurrence of unwanted side effects in the gastrointestinal tract, i.e. the esophagus, stomach, intestines, and rectum, particularly the esophagus, relative to treatment with a nitrogen-containing bisphosphonate alone. Nonlimiting examples of adverse gastrointestinal effects include, but are not limited to those selected from the group consisting of esophagitis, esophageal ulcers, esophageal irritation, esophageal perforation, abdominal pain, gastric duodenal ulcers, and constipation.

In the present invention it is an object to inhibit bone resorption, or more specifically to inhibit undesired or abnormal bone resorption. The term "abnormal bone resorption", as used herein means a degree of bone resorption that exceeds the degree of bone formation, either locally, or in the skeleton as a whole. Alternatively, "abnormal bone resorption" can be associated with the formation of bone having an abnormal structure, as in Paget's disease.

The term "bone resorption inhibiting", as used herein, means preventing bone resorption by the direct or indirect alteration of osteoclast formation or activity. Inhibition of bone resorption refers to prevention of bone loss, especially the inhibition of removal of existing bone either from the mineral phase and/or the organic matrix phase, through direct or indirect alteration of osteoclast formation or activity.

The term "until the desired therapeutic effect is achieved", as used herein, means that the therapeutic agent or agents are continuously administered, according to the dosing schedule chosen, up to the time that the clinical or medical effect sought for the disease or condition being treated is observed by the clinician or researcher. For methods of treatment of the present invention, the pharmaceutical composition is continuously administered until the desired change in bone mass or structure is observed. In such instances, achieving an increase in bone mass or a replacement of abnormal bone structure with normal bone structure are the desired objectives. For methods of prevention of the present invention, the pharmaceutical composition is continuously administered for as long as necessary to prevent the undesired condition. In such instances, maintenance of bone mass density is often the objective. Nonlimiting examples of administration periods can range from about 2 weeks to the remaining lifespan of the mammal. For humans, administration periods can range from about 2 weeks to the remaining lifespan of the human, preferably from about 2 weeks to about 20 years, more preferably from about 1 month to about 20 years, more preferably from about 6 months to about 10 years, and most preferably from about 1 year to about 10 years.

The term "nitrogen-containing" as used herein means that the bisphosphonate compound or pharmaceutically acceptable salt thereof comprises at least one nitrogen atom in the bisphosphonate portion of the molecule. In other words, for a pharmaceutically-acceptable salt of the bisphosphonate, any nitrogen atom contained in the positive counter ion of such a salt, e.g., the nitrogen atom of an ammonium counter ion, would not be considered in meeting the "nitrogen-containing" definition. For example, alendronic acid, i.e. 4-amino-1-hydroxybutylidene-1,1-bisphosphonic acid is an example of a nitrogen-containing bisphosphonate. However, the ammonium salt of the unsubstituted 1-hydroxybutylidene-1,1-bisphosphonic acid would not be a nitrogen-containing bisphosphonate as defined herein.

Compositions of the Present Invention

The pharmaceutical compositions of the present invention comprise a pharmaceutically effective amount of a nitrogen-containing bisphosphonate or a pharmaceutically-acceptable salt thereof and a pharmaceutically effective amount of an isoprenoid compound. These compositions are useful for inhibiting bone resorption in a mammal in need thereof while counteracting the potentially adverse effects, such as gastrointestinal effects, that can be associated with the administration of the bisphosphonate.

Nitrogen-Containing Bisphosphonates

The nitrogen-containing bisphosphonates useful herein correspond to the chemical formula

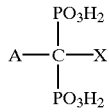

wherein
A and X are independently selected from the group consisting of H, OH, OR, halogen, $NH_2$, NNR, $NR_2$, SR, SH, C1–C30 alkyl (including straight, branched, and cyclic alkyl), substituted C1–C30 alkyl (including straight, branched, and cyclic alkyl), and C5–C14 aryl, wherein said substituted C1–C30 alkyl comprises one or more moieties selected from the group consisting of OH, OR, halogen, $NH_2$, NHR, $NR_2$, SH, SR, and C5–C14 aryl, wherein R is selected from the group consisting of C1–C30 alkyl (including straight, branched, and cyclic alkyl) and C5–C14 aryl, with the proviso that the resulting bisphosphonate compound contains at least one nitrogen atom. In the bisphosphonate compounds of the present invention, A and X can be taken together to form a cyclic moiety. It is also intended that any of the alkyl groups can be unsaturated with a double or triple bond at one or more positions.

Nonlimiting examples of the substituents for the substituted C1–C30 alkyl moiety include those selected from the group consisting of amino, alkylamino, dialkylamino, imidazolyl, pyridyl, imidazonyl, imidazopyridinyl, furanyl, and cycloalkylamino.

The term "aryl," as used herein, refers to a monocyclic or polycyclic system comprising at least one aromatic ring, wherein the monocylic or polycyclic system contains 0, 1, 2, 3, or 4 heteroatoms chosen from N, O, or S, and wherein the monocyclic or polycyclic system is either unsubstituted or substituted with one or more groups independently selected from hydrogen, halogen, $C_{1-10}$ alkyl, $C_{3-8}$ cycloalkyl, aryl, aryl $C_{1-8}$ alkyl, amino, amino $C_{1-8}$ alkyl, $C_{1-3}$ acylamino, $C_{1-3}$ acylamino $C_{1-8}$ alkyl, $C_{1-6}$ alkylamino, $C_{1-6}$ alkylamino $C_{1-8}$ alkyl, $C_{1-6}$ dialkylamino, $C_{1-6}$ dialkylamino-$C_{1-8}$ alkyl, $C_{1-4}$ alkoxy, $C_{1-4}$ alkoxy $C_{1-6}$ alkyl, hydroxycarbonyl, $C_{1-6}$ alkyl, $C_{1-5}$ alkoxycarbonyl, $C_{1-3}$ alkoxycarbonyl $C_{1-6}$ alkyl, hydroxycarbonyl $C_{1-6}$ alkyloxy, hydroxy, hydroxy $C_{1-6}$ alkyl, cyano, trifluoromethyl, oxo or $C_{1-5}$ alkylcarbonyloxy. Examples of aryl include, but are not limited to, phenyl, naphthyl, pyridyl, pyrazinyl, pyrimidinyl, imidazolyl, benzimidazolyl, indolyl, thienyl, furyl, dihydrobenzofuryl, benzo(1,3) dioxolane, oxazolyl, isoxazolyl and thiazolyl.

Preferred nitrogen-containing bisphosphonates are those in which A is selected from the group consisting of H, OH, and halogen, more preferably OH, and X is selected from the group consisting of $NH_2$, NHR, $NR_2$, C5–C14 aryl, substituted C1–C30 alkyl (including straight, branched, and cyclic alkyl) wherein said substituted alkyl group is substituted with one or more moieties selected from the group consisting of OH, OR, halogen, $NH_2$, NHR, $NR_2$, SH, SR, and C5–C14 aryl, with the proviso that the resulting compound contains at least one nitrogen atom.

Most preferred is when A is OH and X is a 3-aminopropyl moiety, so that the resulting compound is a 4-amino-1-hydroxybutylidene-1,1-bisphosphonate, i.e. alendronate.

Pharmaceutically acceptable salts and derivatives of the nitrogen-containing bisphosphonates are also useful herein. Nonlimiting examples of salts include those selected from the group consisting of alkali metal, alkaline metal, ammonium, and mono-, di, tri-, or tetra-C1–C30-alkyl-substituted ammonium. Preferred salts are those selected from the group consisting of sodium, potassium, calcium, magnesium, and ammonium salts. Typically, the salts are formed when one or more of the hydrogen atoms of the phosphonate groups are substituted.

Nonlimiting examples of derivatives include those selected from the group consisting of esters and amides.

Various hydrated and anhydrous forms of the nitrogen-containing bisphosphonates are intended as within the scope of the present invention.

"Pharnaceutically-acceptable" as used herein means that the salts and derivatives of the nitrogen-containing bisphosphonates have the same general pharmacological properties as the free acid form from which they are derived and are acceptable from a toxicity standpoint.

It should be noted that the terms "bisphosphonate" and "bisphosphonates", as used herein in referring to the nitrogen-containing bisphosphonates are meant to also encompass the terms diphosphonates, biphosphonic acids, and diphosphonic acids, as well as salts and derivatives of these materials. The use of a specific nomenclature in referring to the bisphosphonate or bisphosphonates is not meant to limit the scope of the present invention, unless specifically indicated. Because of the mixed nomenclature currently in use by those or ordinary skill in the art, reference to a specific weight or percentage of a bisphosphonate compound in the present invention is on an acid active weight basis, unless indicated otherwise herein. For example, the phrase "about 10 mg of a nitrogen-containing bisphosphonate selected from the group consisting of alendronate, pharmaceutically acceptable salts thereof, and mixtures thereof, on an alendronic acid active weight basis" means that the amount of the bisphosphonate compound selected is calculated based on 10 mg of alendronic acid.

Nonlimiting examples of nitrogen-containing bisphosphonates useful herein include the following:

Alendronic acid, 4-amino-1-hydroxybutylidene-1,1-bisphosphonic acid.

Alendronate (also known as alendronate sodium or monosodium trihydrate), 4-amino-1-hydroxybutylidene-1,1-bisphosphonic acid monosodium trihydrate.

Alendronic acid and alendronate are described in U.S. Pat. No. 4,922,007, to Kieczykowski et al., issued May 1, 1990, and U.S. Pat. No. 5,019,651, to Kiecykowski, issued May 28, 1991, both of which are incorporated by reference herein in their entirety.

Cycloheptylaminomethylene-1,1-bisphosphonic acid, YM 175, Yamanouchi (cimadronate), as described in U.S. Pat. No. 4,970,335, to Isomura et al., issued Nov. 13, 1990, which is incorporated by reference herein in its entirety.

1-hydroxy-3-(1-pyrrolidinyl)-propylidene-1,1-bisphosphonic acid (EB-1053).

1-hydroxy-3-(N-methyl-N-pentylamino)propylidene-1,1-bisphosphonic acid, also known as BM-210955, Boehringer-Mannheim (ibandronate), is described in U.S. Pat. No. 4,927,814, issued May 22, 1990, which is incorporated by reference herein in its entirety.

6-amino-1-hydroxyhexylidene-1,1-bisphosphonic acid (neridronate).

3-(dimethylamino)-1-hydroxypropylidene-1,1-bisphosphonic acid (olpadronate).

3-amino-1-hydroxypropylidene-1,1-bisphosphonic acid (pamidronate).

[2-(2-pyridinyl)ethylidene]-1,1-bisphosphonic acid (piridronate) is described in U.S. Pat. No. 4,761,406, which is incorporated by reference in its entirety.

1-hydroxy-2-(3-pyridinyl)-ethylidene-1,1-bisphosphonic acid (risedronate).

1-hydroxy-2-(1H-imidazol-1-yl)ethylidene-1,1-bisphosphonic acid (zolendronate).

[1-hydroxy-2-imidazo-(1,2-a)pyridin-3-ylethylidene]bisphosphonate (Yamanouchi YH 529).

Preferred are bisphosphonates selected from the group consisting of alendronate, cimadronate, ibandronate, risedronate, piridronate, pamidronate, zolendronate, pharmaceutically acceptable salts thereof, and mixtures thereof.

More preferred is alendronate, pharmaceutically acceptable salts thereof, and mixtures thereof.

Most preferred is alendronate monosodium trihydrate.

It is recognized that mixtures of two or more of the nitrogen-containing bisphosphonates can be utilized.

The precise dosage of the nitrogen-containing bisphosphonate will vary with the dosing schedule, the particular bisphosphonate chosen, the age, size, sex and condition of the mammal or human, the nature and severity of the disorder to be treated, and other relevant medical and physical factors. Thus, a precise pharmaceutically effective amount cannot be specified in advance and can be readily determined by the caregiver or clinician. Appropriate amounts can be determined by routine experimentation from animal models and human clinical studies. Generally, an appropriate amount of nitrogen-containing bisphosphonate is chosen to obtain a bone resorption inhibiting effect, i.e. a bone resorption inhibiting amount of the nitrogen-containing bisphosphonate is administered. For humans, an effective oral dose of nitrogen-containing bisphosphonate is typically from about 1.5 to about 6000 μg/kg body weight and preferably about 10 to about 2000 μg/kg of body weight.

For the nitrogen-containing bisphosphonate, alendronate monosodium trihydrate, common human doses which are administered are generally in the range of about 2 mg/day to about 40 mg/day, preferably about 5 mg/day to about 40 mg/day. In the U.S. presently approved dosages for alendronate monosodium trihydrate are 5 mg/day for preventing osteoporosis, 10 mg/day for treating osteoporosis, and 40 mg/day for treating Paget's disease.

In alternative dosing regimens, the nitrogen-containing bisphosphonate can be administered at intervals other than daily, for example once-weekly dosing, twice-weekly dosing, biweekly dosing, and twice-monthly dosing. In such dosing regimens, appropriate multiples of the bisphosphonate dosage would be administered. For example, in a once weekly dosing regimen, alendronate monosodium trihydrate would be administered at dosages of 35 mg/week or 70 mg/week in lieu of seven consecutive daily dosages of 5 mg or 10 mg.

The pharmaceutical compositions herein comprise from about 1 mg to about 100 mg of nitrogen-containing bisphosphonate, preferably from about 2 mg to 70 mg, and more preferably from about 5 mg to about 70, on a bisphosphonic acid basis. For the bisphosphonate alendronate monosodium trihydrate, the pharmaceutical compositions useful herein comprise about 2.5 mg, 5 mg, 10 mg, 35, mg, 40 mg, or 70 mg of the active on an alendronic acid active weight basis.

Isoprenoid Compounds

The compositions of the present invention comprise a pharmaceutically effective amount of an isoprenoid compound.

The isoprenoid compounds useful herein correspond to the chemical formula

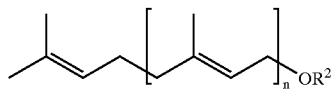

wherein $R^2$ is selected from the group consisting of H (i.e. geranylgeraniol), C1–C30 alkyl (including straight, branched, and cyclic alkyl), C2–C30 alkenyl (including straight, branched, and cyclic alkenyl), C2–C30 alkynyl (including straight, branched, and cyclic alkynyl), C5–C14 aryl, $PO_3H_2$ (i.e. geranylgeranyl phosphate), $P_2O_7H_3$ (i.e. geranylgeranyl pyrophosphate), C=O—$R^3$ (i.e. esters), wherein $R^3$ is selected from the group consisting of H, C1–C10 alkyl (including straight, branched, and cyclic alkyl), C2–C10 alkenyl (including straight, branched, and cyclic alkenyl), C2–C10 alkynyl (including straight, branched, and cyclic alkynyl), C2–C10 hydroxy-substituted alkyl (including straight, branched, and cyclic), C2–C10 amino-substituted alkyl (including straight, branched, and cyclic), C2–C10 carbonylhydroxy-substituted alkyl (including straight, branched, and cyclic), and C5–C14 aryl, and n is an integer from 0 to 3.

Preferably $R^2$ is selected from the group consisting of H, $PO_3H_2$, $P_2O_7H_3$, and C=O—$R^3$, wherein $R^3$ is selected from the group consisting of H, C1–C10 alkyl, C2–C10 hydroxy-substituted alkyl, C2–C10 amino-substituted alkyl, C2–C10 carbonylhydroxy-substituted alkyl, and C5–C14 aryl, and n is an integer from 2 to 3.

More preferably $R^2$ is selected from the group consisting of H, $PO_3H_2$, $P_2O_7H_3$, and C=O—$R^3$, wherein $R^3$ is selected from the group consisting of H, C1–C10 alkyl, C2–C10 hydroxy-substituted alkyl, C2–C10 amino-substituted alkyl, C2–C10 carbonylhydroxy-substituted alkyl, and C5–C14 aryl, and n is 3.

The term "aryl," as used herein, refers to a monocyclic or polycyclic system comprising at least one aromatic ring, wherein the monocyclic or polycyclic system contains 0, 1, 2, 3, or 4 heteroatoms chosen from N, O, or S, and wherein the monocyclic or polycyclic system is either unsubstituted or substituted with one or more groups independently selected from hydrogen, halogen, $C_{1-10}$ alkyl, $C_{3-8}$ cycloalkyl, aryl, aryl $C_{1-8}$ alkyl, amino, amino $C_{1-8}$ alkyl, $C_{1-3}$ acylamino, $C_{1-3}$ acylamino $C_{1-8}$ alkyl, $C_{1-6}$ alkylamino, $C_{1-6}$ alkylamino $C_{1-8}$ alkyl, $C_{1-6}$ dialkylamino, $C_{1-6}$ dialkylamino-$C_{1-8}$ alkyl, $C_{1-4}$ alkoxy, $C_{1-4}$ alkoxy $C_{1-6}$ alkyl, hydroxycarbonyl, hydroxycarbonyl $C_{1-6}$ alkyl, $C_{1-5}$ alkoxycarbonyl, $C_{1-3}$ alkoxycarbonyl $C_{1-6}$ alkyl, hydroxycarbonyl $C_{1-6}$ alkyloxy, hydroxy, hydroxy $C_{1-6}$ alkyl, cyano, trifluoromethyl, oxo or $C_{1-5}$ alkylcarbonyloxy. Examples of aryl include, but are not limited to, phenyl, naphthyl, pyridyl, pyrazinyl, pyrimidinyl, imidazolyl, benzimidazolyl, indolyl, thienyl, furyl, dihydrobenzofuryl, benzo(1,3) dioxolane, oxazolyl, isoxazolyl and thiazolyl.

The esters are also intended to encompass esters of substituted acids such as lactic acid, amino acids, and other complex acids, and mono and higher esters of di and higher carboxylic acids such as succinic acid and glutaric acid.

Preferred isoprenoid compounds are selected from the group consisting of 3,3-dimethyl-2-butan-1-ol, 3,3-diemthyl-2-butyl ethyl ether, dimethylallyl phosphate, dimethylallyl pyrophosphate, 3,3-dimethyl-2-butyl acetate, 3,3-dimethyl2-butyl proprionate, 3,3-dimethyl-2-butyl benzoate, 3,3-dimethyl-2-butyl lactate, 3,3-dimethyl-2-butyl succinate, 3,3-dimethyl-2-butyl succinate, 3,3-dimethyl-2-butyl glutarate, geraniol, geranyl ethyl ether, geranyl phosphate, geranyl pyrophosphate, geranyl acetate, geranyl propionate, geranyl benzoate, geranyl lactate, geranyl succinate, geranyl glutarate, farnesol, farnesyl ethyl ether, farnesyl phosphate, farnesyl pyrophosphate, farnesyl acetate, farnesyl propionate, farnesyl benzoate, farnesyl lactate, farnesyl succinate, farnesyl glutarate, geranylgeraniol, geranylgeranyl ethyl ether, geranylgeranyl phosphate, geranylgeranyl pyrophosphate, geranylgeranyl acetate, geranylgeranyl propionate, geranylgeranyl benzoate, geranylgeranyl lactate, geranylgeranyl succinate, geranylgeranyl glutarate, and mixtures thereof.

More preferred are geranylgeraniol, geranylgeranyl phosphate, geranylgeranyl pyrophosphate, geranylgeranyl acetate, geranylgeranyl propionate, geranylgeranyl benzoate, geranylgeranyl lactate, geranylgeranyl succinate, geranylgeranyl glutarate, and mixtures thereof.

Even more preferred herein are geranylgeraniol, geranylgeranyl pyrophosphate, and mixtures thereof.

It is recognized that mixtures of two or more of the isoprenoid compounds can be utilized.

The precise dosage of the isoprenoid compouds will also vary with the dosing schedule, the particular compound chosen, the age, size, sex and condition of the mammal or human, the nature and severity of the disorder to be treated, and other relevant medical and physical factors. Thus, a precise pharmaceutically effective amount cannot be specified in advance and can be readily determined by the caregiver or clinician. Appropriate amounts can be determined by routine experimentation from animal models and human clinical studies. Generally, an appropriate amount is chosen to obtain an inhibition of the potentially adverse gastrointestinal effects of the nitrogen-containing bisphosphonate. The amount should be below that level which will inhibit the desired bone resorption inhibiting effect of the nitrogen-contianing bisphosphonate. For humans, an effective oral dose of the isoprenoid compound is typically chosen so as to provide a local concentration in the esophagus from about 1 $\mu$M to about 100 $\mu$M, preferably about 10 $\mu$M, although other ranges can be used. Nonlimiting exemplary doses are about 1 ug/kg to about 100 ug/kg, preferably about 10 ug/kg, for a human subject.

For the isoprenoid compound, human doses which can be administered are generally in the range of about 0.1 mg/day to about 10 mg/day, preferably from about 0.25 mg/day to about 5 mg/day, and more preferably from about 0.5 mg/day to about 1.5 mg/day, based on a geranylgeraniol active weight basis. A typical nonlimiting dosage amount would be about 0.75 mg/day. The pharmaceutical compositions herein comprise from about 0.1 mg to about 10 mg, preferably from about 0.25 mg to about 5 mg, and more preferably from about 0.5 mg to about 1.5 mg of the isoprenoid compound. A typical nonlimiting amount for is about 0.75 mg.

Other Components of the Pharmaceutical Compositions

The nitrogen-containing bisphosphonate and the isoprenoid compound are typically administered in admixture with suitable pharmaceutical diluents, excipients, or carriers, collectively referred to herein as "carrier materials", suitably selected with respect to oral administration, i.e. tablets, capsules, elixirs, syrups, powders, and the like, and consistent with conventional pharmaceutical practices. For example, for oral administration in the form of a tablet, capsule, or powder, the active ingredient can be combined with an oral, non-toxic, pharmaceutically acceptable inert carrier such as lactose, starch, sucrose, glucose, methyl cellulose, magnesium stearate, mannitol, sorbitol, croscarmellose sodium and the like; for oral administration in liquid form, e.g., elixirs and syrups, the oral drug components can be combined with any oral, non-toxic, pharmaceutically acceptable inert carrier such as ethanol, glycerol, water and the like. Moreover, when desired or necessary, suitable binders, lubricants, disintegrating agents and coloring agents can also be incorporated. Suitable binders can include starch, gelatin, natural sugars such a glucose, anhydrous lactose, free-flow lactose, beta-lactose, and corn sweeteners, natural and synthetic gums, such as acacia, guar, tragacanth or sodium alginate, carboxymethyl cellulose, polyethylene glycol, waxes, and the like. Lubricants used in these dosage forms include sodium oleate, sodium stearate, magnesium stearate, sodium benzoate, sodium acetate, sodium chloride and the like. A particularly preferred tablet formulation for alendronate monosodium trihydrate is that described in U.S. Pat. No. 5,358,941, to Bechard et al, issued Oct. 25, 1994, which is incorporated by reference herein in its entirety. The compounds used in the present method can also be coupled with soluble polymers as targetable drug carriers. Such polymers can include polyvinylpyrrolidone, pyran copolymer, polyhydroxylpropyl-methacrylamide, and the like.

Methods of the Present Invention

The present invention comprises methods for treating abnormal bone resorption in mammals. The present invention also comprises methods for preventing abnormal bone resorption in mammals. In preferred embodiments of the present invention, the mammal is a human.

The methods and compositions of the present invention are useful for both treating and preventing abnormal bone resorption and conditions associated therewith. Conditions associated with abnormal bone resorption include both generalized and localized bone loss. Also, the creation of bone having an abnormal structure, as in Paget's disease, can be associated with abnormal bone resorption. The term "generalized bone loss" means bone loss at multiple skeletal sites or throughout the skeletal system. The term "localized bone loss" means bone loss at one or more specific, defined skeletal sites.

Generalized boss loss is often associated with osteoporosis. Osteoporosis is most common in post-menopausal women, wherein estrogen production has been greatly diminished. However, osteoporosis can also be steroid-induced and has been observed in males due to age. Osteoporosis can be induced by disease, e.g. rheumatoid arthritis, it can be induced by secondary causes, e.g., glucocorticoid therapy, or it can come about with no identifiable cause, i.e. idiopathic osteoporosis. In the present invention, preferred methods include the treatment or prevention of abnormal bone resorption in osteoporotic humans.

Localized bone loss has been associated with periodontal disease, with bone fractures, and with periprosthetic osteolysis (in other words where bone resorption has occured in proximity to a prosthetic implant).

Generalized or localized bone loss can occur from disuse, which is often a problem for those confined to a bed or a wheelchair, or for those who have an immobilized limb set in a cast or in traction.

The methods and compositions of the present invention are useful for treating and or preventing the following conditions or disease states: osteoporosis, which can include post-menopausal osteoporosis, steroid-induced osteoporosis, male osteoporosis, disease-induced osteoporosis, idiopathic osteoporosis; Paget's disease; abnormally increased bone turnover; osteomalacia; periodontal disease; localized bone loss associated with periprosthetic osteolysis; and bone fractures.

The compositions and methods of the present invention are administered and carried out until the desired therapeutic effect is achieved.

In the methods of the present invention the nitrogen-containing bisphosphonate and the isoprenoid compound are generally administered concurrently. In alternate embodiments, the nitrogen-containing bisphosphonate and the isoprenoid compound can be administered sequentially. Preferably, the isoprenoid compound is administered first.

The following Examples are presented to better illustrate the invention.

EXAMPLE 1

Method for Evaluating the Effect of a Nitrogen-Containing Bisphosphonate and an Isoprenoid Compound on Kinase Activities in Cultured Osteoclasts Murine co-cultures of osteoblasts and marrow cells are prepared using the methods of Wesolowski, et al., *Exp Cell Res,* (1995), 219, pp. 679–686, which is incorporated by reference herein in its entirety. Bone marrow cells are harvested from 6-week-old male Balb/C mice by flushing marrow spaces of freshly isolated long bones (tibiae and femora) with α-MEM (minimal essential media) containing penicillin/streptomycin (100 I.U./ml of each and 20 mM Hepes buffer). The bone marrow cells are suspended in α-MEM and the cells are filtered through an approximately 70 μm cell strainer. The filtrate is centrifuged at about 300×g for about 7 minutes. The resulting pellet is resuspended in α-MEM supplemented with fetal calf serum (10% v/v) and 10 nM 1, 25-$(OH)_2$ vitamin $D_3$. These bone marrow isolates are added to sub-confluent monolayers of osteoblastic MB 1.8 cells in cell culture plates and cultured for 7 days at 37□ C. in the presence of 5% $CO_2$. Culture media is replenished ever other day. Fusion of the osteoclast precursor cells from bone marrow (with each other) to form multinucleated osteoclast-like cells typically occurs after about 7 days. Osteoclast-like cells are enriched by sequential treatment with collagenase (1 mg/mL in phosphate buffered saline) for one hour at 37° C. and EDTA (0.2 g/L in phosphate buffered saline) for 20 min at 37° C. Non-adherent cells are rinsed away by washing with phosphate buffered saline. Osteoclast-like cells which are resistant to the sequential treatments are present at about 95% purity and are maintained in α-MEM supplemented with fetal calf serum (10% v/v), 10 nM 1,25-$(OH)_2$ vitamin $D_3$, macrophage-colony-stimulating factor (5 ng/mL).

The compounds to be evaluated are prepared as a solution of the desired concentration in α-MEM. Examples of compounds that can be evaluated include nitrogen-containing bisphosphonates such as alendronate monosodium trihydrate, as well as compounds that block the effects of these inhibitors, such as isoprenoid compounds, for example, geranylgeraniol, geranylgeranyl phosphate, geranylgeranyl pyrophosphate, geranylgeranyl acetate, geranylgeranyl propionate, geranylgeranyl benzoate, geranylgeranyl lactate, geranylgeranyl succinate, and geranylgeranyl glutarate. Combinations of compounds can also be evaluated. The solutions of the compounds to be evaluated are added to the cultures for a time period of 17–24 hours. No treatment controls (controls not treated with compounds) are prepared by adding equivalent volumes of α-MEM to the control dishes.

Cells are then harvested and lysed in a HEPES (N-(2-hydroxyethyl)piperazine-N'-(2-ethansulfonic acid) or Tris buffer containing the following: β-glycerophosphate (50 mM); $Na_3VO_4$ (1 mM); NaF (1 mM); Microcystin LR (1 μM); leupeptin (10 μg/ml); aprotinin (10 μg/ml); phenylmethyl sulfonylfluoride (1 mM). Protein concentrations are determined for each lysate and 5–20 μg are loaded into each lane of a SDS-PAGE (sodium dodecyl sulfate-polyacrylamide gel electrophoresis) gel containing Myelin Basic Protein, or another kinase substrate, which has been polymerized into the gel at a concentration between 50–400 μg/ml. Molecular weight standards are also loaded into one or more lanes of the gels. In-gel kinase assays are run according to a standard procedure based on Kameshita and Fujisawa, 1989 (Anal. Biochem. 183:139–143) and of Gotoh et al., 1990 (Eur. J. Biochem. 193: 661–669), both references being incorporated by reference herein in their entirety. The proteins are electrophoresed in the above gels. The gels are then successively soaked in 50 mM HEPES, pH 7.6; 5 mM 2-mercaptoethanol and each of the following (for each wash): (a) 20% isopropanol; (b) no additions; (c) urea (6 M); (d) Urea (3 M); (e) Urea (0.75 M); and Tween 20 (0.05% vol:vol). Kinase reactions are then run by first soaking the gels in 20 mM HEPES, pH 7.6; 20 mM $MgCl_2$; 2 mM DTT and then in the same buffer containing 0.02 M ATP (non-radioactive) with ca. 1000 cpm/pmol $^{32}P$-γ-ATP. The gels are then washed six times with 5% trichloroacetic acid and 1% pyrophosphate. The gels are then stained with Coomassie brilliant blue dye (0.125%) in 50% methanol, 10% acetic acid; destained with 30% methanol, 10% acetic acid; soaked in 2% glycerol; and dried using a gel dryer. The gels are then exposed to autoradiography film for times ranging from several hours to weeks. The bands observed in the autoradiographs representing the gels reflect kinase activities. Mst 1 (apparent molecular weight about 59 kDa), Mst 2 (apparent molecular weight about 60 kDa), and a 34 kDa Mst kinase fragment are observed and identified by their migration as compared to the migration of molecular weight standards. The band intensities on the autoradiography film are quantitated by densitometry and comparisons between bands from untreated controls and bands from echistatin-treated cells provide the basis for the analyses.

EXAMPLE 2
Pharmaceutical Tablet Compositions

Tablets are prepared using standard mixing and formation techniques as described in U.S. Pat. No. 5,358,941, to Bechard et al., issued Oct. 25, 1994, which is incorporated by reference herein in its entirety.

Tablets containing about 10 mg of alendronate monosodium trihydrate, on an alendronic acid active basis, and about 0.75 mg of geranylgeraniol, are prepared using the following relative weights of ingredients.

| Ingredient | Per Tablet | Per 4000 Tablets |
|---|---|---|
| Alendronate Monosodium Trihydrate | 13.051 mg | 52.20 g |
| Geranylgeraniol | 0.75 mg | 3.00 g |
| Anhydrous Lactose, NF | 71.32 mg | 285.28 g |
| Microcrystalline Cellulose, NF | 80.0 mg | 320.0 g |
| Magnesium Stearate, NF | 1.0 mg | 4.0 g |
| Croscarmellose Sodium, NF | 2.0 mg | 8.0 g |

The resulting tablets are useful for administration in accordance with the methods of the present invention for treating or preventing bone resorption.

Similarly, tablets comprising other relative weights of alendronate, on an alendronic acid active weight basis are prepared. Also, tablets containing other nitrogen-containing bisphosphonates, or mixtures thereof, at appropriate active levels are similarly prepared: e.g., cimadronate, ibandronate, risedronate, piridronate, pamidronate, zolendronate, and pharmaceutically acceptable salts thereof. Also, tablets containing combinations of bisphosphonates are similarly prepared.

Similarly, tablets comprising other isoprenoid compounds or mixtures thereof are prepared, for example 3,3-dimethyl-2-butan-1-ol, 3,3-diemthyl-2-butyl ethyl ether, dimethylallyl phosphate, dimethylallyl pyrophosphate, 3,3-dimethyl-2-butyl acetate, 3,3-dimethyl2-butyl proprionate, 3,3-dimethyl-2-butyl benzoate, 3,3-dimethyl-2-butyl lactate, 3,3-dimethyl-2-butyl succinate, 3,3-dimethyl-2-butyl succinate, 3,3-dimethyl-2-butyl glutarate, geraniol, geranyl ethyl ether, geranyl phosphate, geranyl pyrophosphate, geranyl acetate, geranyl propionate, geranyl benzoate, geranyl lactate, geranyl succinate, geranyl glutarate, farnesol, farnesyl ethyl ether, farnesyl phosphate, farnesyl pyrophosphate, farnesyl acetate, farnesyl propionate, farnesyl benzoate, farnesyl lactate, farnesyl succinate, farnesyl glutarate, geranylgeraniol, geranylgeranyl ethyl ether, geranylgeranyl phosphate, geranylgeranyl pyrophosphate, geranylgeranyl acetate, geranylgeranyl propionate, geranylgeranyl benzoate, geranylgeranyl lactate, geranylgeranyl succinate, and geranylgeranyl glutarate.

The tablets described herein are useful for inhibiting bone resorption while mitigating potentially adverse gastrointestinal effects.

What is claimed is:

1. A pharmaceutical composition suitable for inhibiting bone resorption in a mammal in a need thereof comprising from about 1 to about 100 mg of a nitrogen-containing bisphosphonate or a pharmaceutically acceptable salt thereof and from about 0.1 to about 10 mg of an isoprenoid compound of the formula:

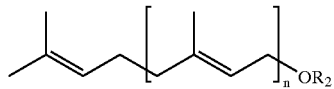

wherein $R^2$ is selected from the group consisting of H, C1–C30 alkyl selected from straight, branched, and cyclic alkyl, C2–C30 alkenyl selected from straight, branched, and cyclic alkenyl, C2–C30 alkynyl selected from straight, branched, and cyclic alkyl, C5–C14 aryl, and C=O—$R^3$, wherein $R^3$ is selected from the group consisting of H, C1–C10 alkyl selected from straight, branched, and cyclic alkyl, C2–C10 alkenyl selected from straight, branched, and cyclic alkenyl C2–C10 alkynyl selected from straight, branched, and cyclic alkynyl, C2–C10 hydroxy-substituted alkyl selected from straight, branched, and cyclic, C2–C10 amino-substituted alkyl selected from straight, branched, and cyclic, C2–C10 carbonylhydroxy-substituted alkyl selected from straight, branched, and cyclic, and C5–C14 aryl, and n is an integer from 0 to 3, wherein the composition being is also suitable for mitigating the gastrointestinal side effects associated with bisphosphonate therapy.

2. A pharmaceutical composition according to claim 1 wherein said nitrogen containing bisphosphonate is selected from the group consisting of alendronate, cimadronate, ibandronate, risedronate, piridronate, pamidronate, zolendronate, pharmaceutically acceptable salts thereof, and mixtures thereof.

3. A pharmaceutical composition according to claim 2 wherein said isoprenoid compound corresponds to the chemical formula

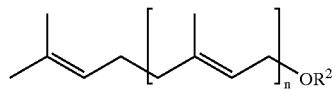

wherein $R^2$ is selected from the group consisting of H, C1–C30 alkyl, C2–C30 alkenyl, C2–C30 alkynyl, C5–C14 aryl, $PO_3H_2$, $P_2O_7H_3$, and —C=O—$R^3$, wherein $R^3$ is selected from the group consisting of H, C1–C10 alkyl, C2–C10 alkenyl, C2–C10 alkynyl, C2–C10 hydroxy-substituted alkyl, C2–C10 amino-substituted alkyl, C2–C10 carbonylhydroxy-substituted alkyl, and C5–C14 aryl, and n is an integer from 0 to 3.

4. A pharmaceutical composition according to claim 3 wherein $R^2$ is selected from the group consisting of H, $PO_3H_2$, $P_2O_7H_3$, and —CO=O—$R^3$, wherein $R^3$ is selected from the group consisting of H, C1–C10 alkyl, C2–C10 hydroxy-substituted alkyl, C2–C10 amino-substituted alkyl, C2–C10 carbonylhydroxy-substituted alkyl, and C5–C14 aryl, and n is an integer from 2 to 3.

5. A pharmaceutical composition according to claim 4 wherein $R^2$ is selected from the group consisting of H, PO$_3$H$_2$, P$_2$O$_7$H$_3$, and —C=O—R$^3$, wherein R$^3$ is selected from the group consisting of H, C1–C10 alkyl, C2–C10 hydroxy-substituted alkyl, C2–C10 amino-substituted alkyl, C2–C10 carbonylhydroxy-substituted alkyl, and C5–C14 aryl, and n is 3.

6. A pharmaceutical composition according to claim 3 wherein said isoprenoid compound is selected from the group consisting of 3,3-dimethyl-2-butan-1-ol, 3,3-diemthyl-2-butyl ethyl ether, dimethylallyl phosphate, dimethylallyl pyrophosphate, 3,3-dimethyl-2-butyl acetate, 3,3-dimethyl2-butyl proprionate, 3,3-dimethyl-2-butyl benzoate, 3,3-dimethyl-2-butyl lactate, 3,3-dimethyl-2-butyl succinate, 3,3-dimethyl-2-butyl succinate, 3,3-dimethyl-2-butyl glutarate, geraniol, geranyl ethyl ether, geranyl phosphate, geranyl pyrophosphate, geranyl acetate, geranyl propionate, geranyl benzoate, geranyl lactate, geranyl succinate, geranyl glutarate, farnesol, farnesyl ethyl ether, farnesyl phosphate, farnesyl pyrophosphate, farnesyl acetate, farnesyl propionate, farnesyl benzoate, farnesyl lactate, farnesyl succinate, farnesyl glutarate, geranylgeraniol, geranylgeranyl ethyl ether, geranylgeranyl phosphate, geranylgeranyl pyrophosphate, geranylgeranyl acetate, geranylgeranyl propionate, geranylgeranyl benzoate, geranylgeranyl lactate, geranylgeranyl succinate, geranylgeranyl glutarate, and mixtures thereof.

7. A pharmaceutical composition according to claim 6 wherein said isoprenoid compound is selected from the group consisting of geranylgeraniol, geranylgeranyl phosphate, geranylgeranyl pyrophosphate, geranylgeranyl acetate, geranylgeranyl propionate, geranylgeranyl benzoate, geranylgeranyl lactate, geranylgeranyl succinate, geranylgeranyl glutarate, and mixtures thereof.

8. A pharmaceutical composition according to claim 7 wherein said isoprenoid compound is selected from the group consisting of geranylgeraniol, geranylgeranyl pyrophosphate, and mixtures thereof.

9. A pharmaceutical composition according to claim 7 wherein said nitrogen-containing bisphosphonate is alendronate and pharmaceutically acceptable salts thereof.

10. A pharmaceutical composition according to claim 9 wherein said nitrogen-containing bisphosphonate is alendronate monosodium trihydrate.

11. The pharmaceutical composition according to claim 1, wherein the bisphosphonate or a pharmaceutically-acceptable salt thereof is present in an amount of from about 2 to about 70 mg and the osprenoid compound is present in an amount of from about 0.1 to about 10 mg.

12. The pharmaceutical composition according to claim 1, wherein the alendronate monosodium trihydrate is present in an amount of from about 1 to about 100 mg, on an alendronic acid weight basis, and the isoprenoid compound, selected from the group consisting of geranylgeraniol, geranylgeranyl pyrophosphate, and mixtures thereof, is present in an amount of from about 0.1 to about 10 mg.

13. The pharmaceutical composition according to claim 1, wherein the alendronate monosodium trihydrate is present in an amount of from about 2 to about 70 mg, on an alendronic acid weight basis, and the isoprenoid, selected from the group consisting of geranylgeraniol, geranylgeranyl pyrophosphate, and mixtures thereof is present in an amount of from bout 0.1 to about 10 mg.

* * * * *